United States Patent [19]

Vaillancourt

[11] Patent Number: 4,961,729

[45] Date of Patent: Oct. 9, 1990

[54] CATHETER INSERTION ASSEMBLY

[76] Inventor: Vincent L. Vaillancourt, 30A Ridgedale Ave., East Hanover, N.J. 07936

[21] Appl. No.: 283,602

[22] Filed: Dec. 13, 1988

[51] Int. Cl.⁵ .............................................. A61M 5/00
[52] U.S. Cl. ..................................... 604/164; 604/168
[58] Field of Search ................ 604/164, 165, 168, 170

[56] References Cited

U.S. PATENT DOCUMENTS

| | | | |
|---|---|---|---|
| 4,306,562 | 12/1981 | Osborne | 604/164 |
| 4,629,450 | 12/1986 | Suzuki et al. | 604/164 |
| 4,652,256 | 3/1987 | Vallancourt | 604/164 |

FOREIGN PATENT DOCUMENTS 0139091  5/1985  European Pat. Off. ............ 604/168

Primary Examiner—Stephen C. Pellegrino

[57] ABSTRACT

The catheter insertion assembly employs an aperture in the wall of the needle near the distal and to communicate with an annular flashback chamber between the needle and the surrounding catheter or a surrounding dilator. The needle may be hollow throughout for passage of a guide wire or may be plugged downstream of the aperture.

3 Claims, 1 Drawing Sheet

CATHETER INSERTION ASSEMBLY

This invention relates to a catheter insertion assembly. More particularly, this invention relates to a catheter insertion assembly having a flashback chamber.

Heretofore, various types of catheter insertion assemblies have been known for implanting a catheter into a blood vessel, such as a vein or artery. In some cases, the insertion assembly has been composed of a catheter and an internally disposed needle. Usually for implantation, the needle first penetrates into the blood vessel to provide an opening through which the catheter can then be inserted. Thereafter, the needle is withdrawn while the catheter remains in place. In some cases, the catheter insertion assemblies have also included a guide wire which is slidably mounted within the needle to facilitate guidance of the needle into a blood vessel.

One of the problems which arises with the implantation of a catheter into a blood vessel is the need to know when the wall of a blood vessel has been penetrated. If this cannot be readily determined, a risk arises that the needle of the insertion assembly may pass through an opposite wall of the blood vessel. Further, complete passage through a blood vessel may result in a coring, cutting or other harmful effect on body tissue, muscle or the like.

In order to obviate this problem, catheter insertion assemblies have been constructed with flashback arrangements so that a physician can determine whether the needle has passed into a vessel. In this respect, the flashback device is constructed so that blood enters the needle and passes into a chamber which is exposed for visual viewing. For example, U.S. Pat. No. 4,317,445 describes a catheter insertion unit with a separate flashback indication for a cannula. In this case, a hollow needle is disposed within a flexible cannular (catheter tube) while a hub proximal to the distal end of the needle is provided with a vented flashback chamber into which blood may flow upon venous entry of the needle. However, with such a construction, the blood flow path is relatively long, that is, extending from the distal end of the hollow needle to the proximally located flashback chamber. Further, because of the resistance imparted by the relatively long flow path, a risk occurs that the needle may pass through the vessel and exit on an opposite side before blood appears in the flashback chamber. In addition, the catheter is provided with a port closely adjacent the distal end to permit blood flow therethrough into a second chamber to provide a visual indication of cannula entry. However, this does not obviate a risk that the needle has not completely penetrated a blood vessel.

U.S. Pat. Nos. 4,464,177 and 4,487,605 describe further catheter insertion assemblies employing flashback chambers. As described in U.S. Pat. No. 4,464,177, the flashback response time is to be accelerated by the use of a syringe in order to create a slight vacuum in the flashback chamber. However, provision must be made to insure that air emboli are not forced through the catheter and into the vascular system of the patient and without causing vascular collapse. U.S. Pat. No. 4,487,605 describes a similar system which employs an elastomeric bladder to create a partial vacuum in a flashback chamber. In either case, the constructions are rather cumbersome to construct and to use.

Aside from the problems of the previously known catheter insertion assemblies, other problems have been presented in practice. For example, venous blood which is most often accessed is under low pressure, for example, about 4 to 8 inches of water in the peripheral veins. Further, near the heart the blood pressure in the major veins is extremely low and may go negative depending upon the position of the patient. Still further, there is a continuing trend to smaller opening needles and catheters which create increased flow resistance. This is a significant limitation in small bore 22 Gage Catheters.

Accordingly, it is an object of the invention to provide a catheter insertion of relatively simple construction.

It is another object of the invention to provide a catheter insertion assembly which is able to give a rapid flashback response.

It is another object of the invention to provide a catheter insertion assembly employing a catheter and needle of relatively small bore while providing rapid flashback reaction time.

It is another objection of the invention to obtain an instantaneous flashback reaction during implantation of a catheter.

Briefly, the invention provides a catheter insertion assembly comprised of an elongated catheter and a needle which is slidably mounted coaxially within the catheter and which is sized to define an annular flashback chamber therebetween. In addition, the needle is provided with a hollow distal end which projects from the catheter for piercing a wall of a vessel and at least one aperture in the needle which communicates the hollow distal end with the annular flashback chamber in order to deliver venous blood thereto.

The aperture which is provided in the needle is positioned a short distance from a needle bevel located at the distal end and just above the tapered distal section of the catheter which slidably receives the needle.

During use, as the needle penetrates a wall of a blood vessel, the pressure of the blood causes the blood to flow into and through the hollow distal end of the needle. At the same time, the aperture in the needle is sized so that the blood also passes into the flashback chamber located between the needle and catheter so as to give a rapid visual indication of the existence of blood therein.

The flow of blood into the flashback chamber can be accelerated by having the needle plugged at a point downstream of the aperture. In this way, the main flow of the blood is forced to flow through the aperture into the flashback chamber.

Since the blood flow from the blood vessel is in a continuous path through the distal end of the needle and, thence, through the aperture into the flashback chamber, the flashback chamber can begin to fill with blood prior to passage of the catheter into the vessel. Thus, the response time for detecting flashback is reduced as compared with structures, for example, as described in U.S. Pat. No. 4,317,445. Thus, the risk of penetrating completely through a blood vessel before insertion of the catheter can be avoided.

In one embodiment, the catheter insertion assembly can be provided with a wire guide which is slidably mounted coaxially within a hollow needle for movement from a rest position upstream of the aperture into the flashback chamber to an extended position projecting from the needle. In this case, the wire guide may be sized so as to virtually fill the lumen of the needle. This enhances the flow of blood through the aperture into the flashback chamber.

The catheter may be made of a transparent or translucent material so as to permit viewing of the blood in the flashback chamber.

In still another embodiment, the catheter insertion assembly may be constructed of a catheter and a tubular dilator mounted coaxially within the catheter. In this case, the needle is slidably mounted within the dilator and is sized to define an annular flashback chamber therebetween. Again, an aperture is provided in a hollow distal end in the needle to communicate with the flashback chamber to deliver venous blood thereto upon penetration of a blood vessel. In this case, the dilator as well as the catheter is made of a clear material so as to permit viewing of the filling of blood into the flashback chamber. The dilator may also be slidably mounted within the catheter so as to permit removal from the catheter after implanting of the catheter.

These and other objects and advantages of the invention will become more apparent from the following detailed description taken in conjunction with the accompanying drawings wherein.

Figure 1:
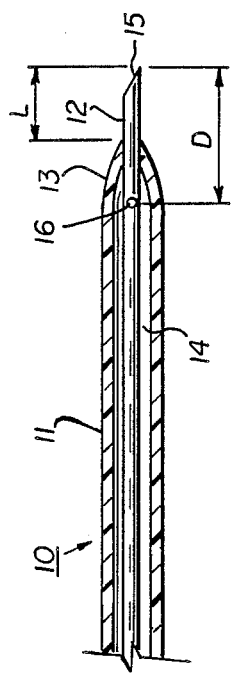
FIG. 1 illustrates a partial view of a catheter insertion assembly constructed in accordance with the invention.

Referring to FIG. 1, the catheter insertion assembly 10 is constructed, in part, of an elongated catheter 11 and a needle 12 which is slidably mounted coaxially within the catheter 11. As indicated, the catheter 11 has a tapered distal end 13 which slidably receives the needle 12 in sealed relation. In addition, the needle 12 is sized to define an annular flashback chamber 14 between the catheter 11 and the needle 12.

The needle 12 has a bevel 15 at the distal end, as is known, as well as a hollow distal end which projects from the catheter 11 in order to pierce a wall of a blood vessel (not shown). In addition, the needle 12 has an aperture 16 within the catheter 11 which communicates the hollow distal end of the needle 12 with the chamber 14 in order to deliver venous blood thereto. As indicated, the center of the aperture 16 is positioned at a distance D from the tip of the bevel 15 which is greater than the exposed length L of the needle 12 from the catheter 11 while being closely adjacent the tapered distal end 13 of the catheter 11.

The remainder of the catheter insertion assembly is of generally known construction and need not be further described.

During use, the bevel end 15 of the needle 12 is penetrated into a wall of a blood vessel. At this time, blood begins to flow into the lumen of the needle 12 under the pressure of the blood in the vessel. The blood then passes through the aperture 16 into the chamber 14 between the catheter 11 and needle 12. This chamber 14 thus provides a flashback chamber 14 for the viewing of the blood therein as an indication that a blood vessel has been penetrated. The amount of time that the blood takes to flow into the flashback chamber 14 after penetration of the needle bevel 15 into the vessel is relatively short. That is, the flashback chamber 14 fills with blood prior to passage of the catheter 11 into the vessel or prior to passage of the needle bevel 15 entirely through the blood vessel.

The catheter 11 is made of any suitable material to permit visual viewing of the blood within the flashback chamber 14. For example, the catheter 11 may be made of a transparent material or of a translucent material.

The size of the needle 12 and of the catheter 11 may be of any suitable size for the purpose intended for the catheter 11. For example, relatively small diameter needle and catheters may be used.

The needle 12 may be hollow throughout or may be plugged at a point downstream of the aperture 16. In this latter case, the plugging of the needle 12 accelerates the response time of the assembly 10 to the penetration of the needle 12 into a blood vessel. That is, the blood is caused to flow into the flashback chamber 14 via the aperture 16 once the limited volume of the hollowed end of the needle has been filled.

Figure 2:
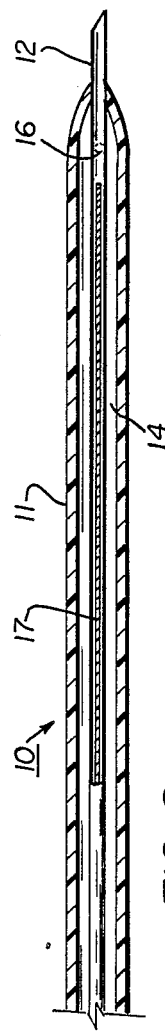
FIG. 2 illustrates a modified catheter insertion assembly according to the invention employing a wire guide.

Referring to FIG. 2, wherein like reference characters indicate like parts as above, the catheter insertion assembly may also be provided with a wire guide 17 which is slidably mounted within the needle 12 for movement from a rest position slightly upstream of the aperture 16 (as shown) to an extended position (not shown) projecting from the needle 12. In this case, the guide wire 17 may be of a size to virtually fill the lumen of the needle 12. The function and purpose of such a wire guide 17 is known and need not be further described.

Figure 3:
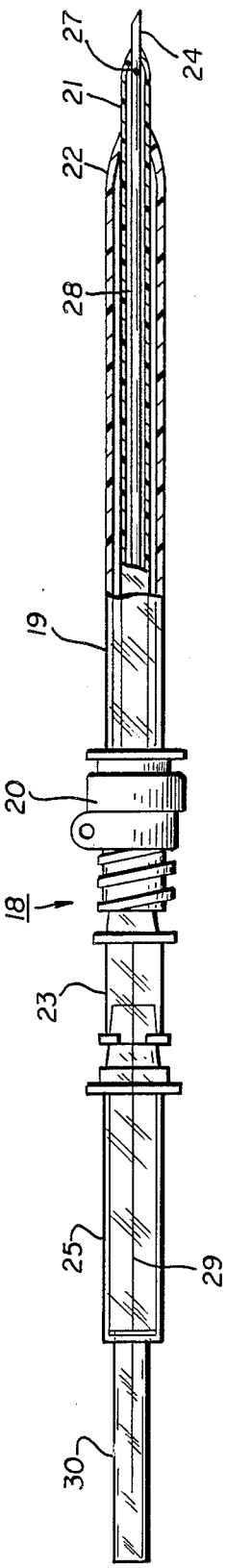
FIG. 3 illustrates a partial cross-sectional view of a catheter insertion assembly constructed in accordance with the invention.

Referring to FIG. 3, the catheter insertion assembly 18 is constructed with a catheter 19 which is mounted on a catheter hub 20 and which is made of any suitable clear material as described above. In addition, a tubular dilator 21 is mounted coaxially within the catheter 19 in slidable relation. As indicated the distal end 22 of the catheter 11 is tapered so as to sealingly engage the dilator 21.

The dilator 21 is mounted in a dilator hub 23 at the proximal end. This dilator hub 23 is movably mounted relative to the catheter hub 20 so that the dilator 21 can be withdrawn from within the catheter 11 when required.

The insertion assembly 18 also employs a hollow needle 24 which is slidably mounted within the dilator 21 and which extends to a needle hub 25 at a proximal end. As indicated, the needle hub 25 is mounted on the dilator hub 23. As above, the needle 24 has an aperture 27 which communicates the hollow interior of the needle 24 with an annular flashback chamber 28 located between the needle 24 and the dilator 21. To this end, the distal end of the dilator 21 sealingly engages the needle 24 for slidable movement of the needle 24 therein.

As indicated in FIG. 3, a wire guide 29 is mounted in a wire guide holder 29 which, in turn, is slidably mounted within the needle hub 25. The wire guide 28 is initially positioned to have a distal end at a rest position upstream of the aperture 27 and is movable to an extended position projecting from the needle 24. In this respect, the wire guide holder 30 can be pushed forwardly into the needle hub 25 in order to expel the wire guide wire 29 when required.

The dilator 21 and catheter 19 are made of any suitable clear material or may be made clear with an X-ray opaque stripe.

The operation of the catheter insertion assembly 18 is similar to that as described above with respect to FIG. 1.

The invention thus provides a catheter insertion assembly which is able to respond almost immediately to the penetration of a needle having a hollow distal end into a blood vessel. In this respect, the flow path for the blood through the needle into a flashback chamber is relatively short. Further, the flow path is of such a length that the flashback chamber can be accessed by the blood flow prior to passage of the needle through a blood vessel and prior to passage of a catheter into a blood vessel.

The invention further provides a catheter insertion assembly which is of relatively simple constructions and which requires relatively parts.

While the needle has been described as having a single aperture, multiple apertures may be provided to enhance the flow of blood into the flashback chamber. For example, for a needle having a lumen of 0.013 inches, the aperture 16 may have a diameter of 0.007 inches. Further examples of the size of the needle, aperture and catheter are of the FIG. 1 embodiment as follows.

| Needle Lumen (I.D.) (Inches) | Aperture (16) (Inches-Diameter) | Catheter Lumen (I.D.) (Inches) |
|---|---|---|
| .011 | .006 | .022 |
| .015 | .010 | .028 |

What is claimed is:

1. A catheter insertion assembly comprising
an elongated catheter;
a tubular dilator mounted coaxially within said catheter;
a needle slidably mounted within said dilator and being sized to define an annular flashback chamber therebetween, said needle having a hollow distal end projecting from said dilator for piercing a wall of a vessel and at least one aperture in said needle communicating said hollow distal end with said annular flashback chamber to deliver venous blood thereto; and a wire guide slidably mounted coaxially within said needle for movement from a rest position upstream of said aperture to an extended position downstream of said aperture and projecting from said needle.

2. A catheter insert assembly as set forth in claim 1 wherein each of said catheter and said dilator is made of clear material.

3. A catheter insert assembly as set forth in claim 1 wherein said dilator is slidably mounted in said catheter.

* * * * *